US00PP32539P2

(12) United States Plant Patent
Hooper

(10) Patent No.: US PP32,539 P2
(45) Date of Patent: Dec. 1, 2020

(54) ***MAGNOLIA* PLANT NAMED 'MGPRO2008'**

(50) Latin Name: ***Magnolia* hybrid**
Varietal Denomination: MGPRO2008

(71) Applicant: Vance James Hooper, Waitara (NZ)

(72) Inventor: Vance James Hooper, Waitara (NZ)

( * ) Notice: Subject to any disclaimer, the term of this patent is extended or adjusted under 35 U.S.C. 154(b) by 0 days.

(21) Appl. No.: 16/873,148

(22) Filed: Feb. 13, 2020

(51) Int. Cl.
*A01H 5/00* (2018.01)
*A01H 6/00* (2018.01)

(52) U.S. Cl.
USPC ..... Plt./223

(58) Field of Classification Search
USPC ..... Plt./223
See application file for complete search history.

*Primary Examiner* — Susan McCormick Ewoldt

(57) ABSTRACT

A new cultivar of *Magnolia* plant named 'MGPRO2008' that is characterized by a compact habit, medium sized leaves, flowers having bright pink tepals and a large number of flowers during the Summer.

2 Drawing Sheets

Botanical classification: *Magnolia* hybrid.
Variety denomination: 'MGPRO2008'.

BACKGROUND OF THE INVENTION

The present invention relates to a new and distinct cultivar of *Magnolia* plant botanically known as *Magnolia* hybrid and hereinafter referred to by the cultivar name 'MGPRO2008'.

The new cultivar is the product of a breeding program conducted by the inventor in a cultivated area of Waitara, New Zealand. The objective of the breeding program is to develop new *Magnolia* cultivars that are smaller in size and have attractive flower colors.

'MGPRO2008' originated from crossing the female or seed parent *Magnolia* hybrid 'Amethyst Flame' (not patented) and the male or pollen parent *Magnolia soulangeana* x *lilliflora* 'Genie' (U.S. Plant Pat. No. 20,748). The crossing was conducted in 2004 in a controlled environment. The cultivar 'MGPRO2008' was selected by the inventor in 2009 as a single plant within the progeny of the stated cross in a cultivated area of Waitara, New Zealand.

Asexual reproduction of the new cultivar 'MGPRO2008' by field budding was first performed in 2009 in Waitara, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Magnolia* cultivar 'MGPRO2008'. These traits in combination distinguish 'MGPRO2008' as a new and distinct cultivar.

1. *Magnolia* 'MGPRO2008' exhibits a compact habit.
2. *Magnolia* 'MGPRO2008' exhibits medium sized leaves.
3. *Magnolia* 'MGPRO2008' exhibits flowers having bright pink tepals.
4. *Magnolia* 'MGPRO2008' exhibits a large number of flowers during the Summer.

The closest comparison variety is *Magnolia* 'Susan' (not patented).

'MGPRO2008' is different than 'Susan' in the following characteristics:

1. *Magnolia* 'MGPRO2008' exhibits a compact habit. In contrast, 'Susan' has a more dense upright habit.
2. *Magnolia* 'MGPRO2008' exhibits medium sized leaves. In contrast, the leaves of 'Susan' are narrower.
3. *Magnolia* 'MGPRO2008' exhibits flowers having bright pink tepals. In contrast, the tepals of 'Susan' are purple-pink.
4. *Magnolia* 'MGPRO2008' exhibits a large number of flowers during the Summer. In contrast, 'Susan' produces a smaller number of flowers during the Summer.

'MGPRO2008' is different than the female parent plant in the following characteristics:

1. *Magnolia* 'MGPRO2008' exhibits a compact habit. In contrast, the female parent plant has a broader habit with spreading branches.
2. *Magnolia* 'MGPRO2008' exhibits medium sized leaves. In contrast, the leaves of the female parent plant are larger.
3. *Magnolia* 'MGPRO2008' exhibits flowers having bright pink tepals. In contrast, the tepals of the female parent plant are red-purple turning to pale purple.
4. *Magnolia* 'MGPRO2008' exhibits a large number of flowers during the Summer. In contrast, the female parent plant produces a smaller number of flowers during the Summer.

'MGPRO2008' is different than the male parent plant in the following characteristics:

1. *Magnolia* 'MGPRO2008' exhibits a compact habit. In contrast, the male parent plant has a more open pyramidal habit.
2. *Magnolia* 'MGPRO2008' exhibits medium sized leaves. In contrast, the leaves of the male parent plant are smaller.
3. *Magnolia* 'MGPRO2008' exhibits flowers having bright pink tepals. In contrast, the tepals of the male parent plant are red.

4. *Magnolia* 'MGPRO2008' exhibits a large number of flowers during the Summer. In contrast, the male parent plant produces a smaller number of flowers during the Summer.

BRIEF DESCRIPTION OF THE DRAWING

The accompanying photographs illustrate the distinguishing traits of *Magnolia* 'MGPRO2008'.

The photograph of FIG. 1 shows an overall view of a 1 year old plant in flower.

Figure 1:
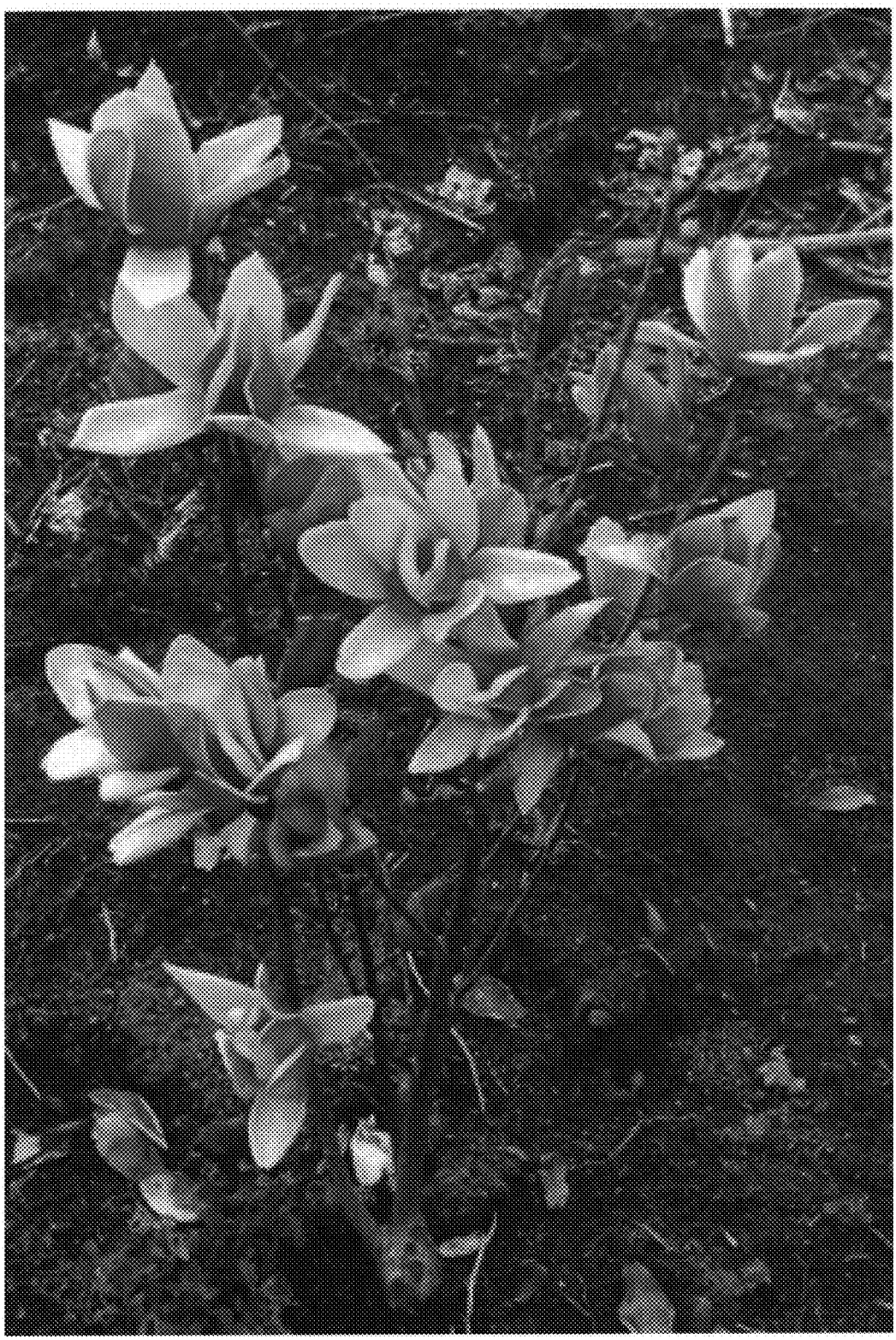
Figure 2:
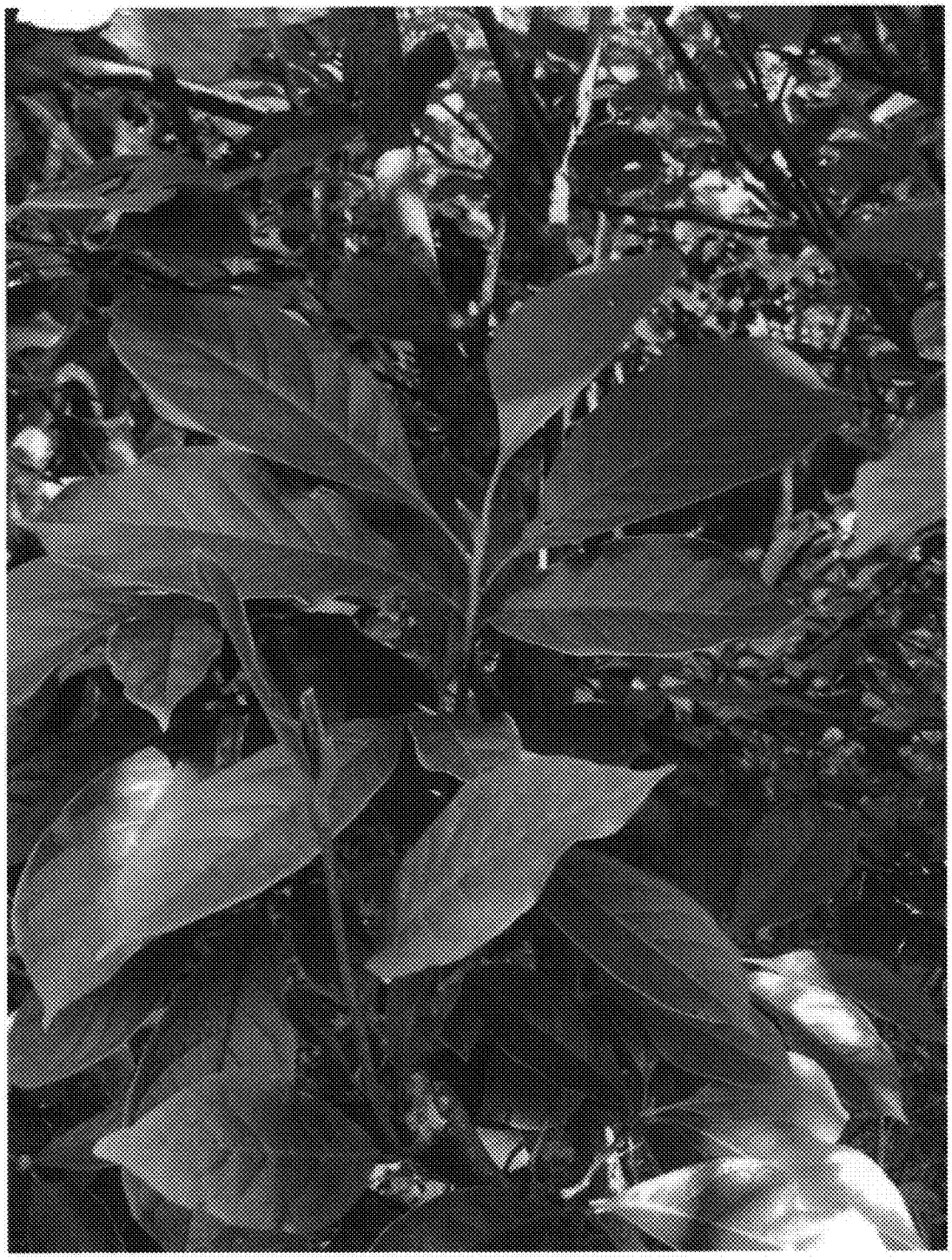

The photograph of FIG. 2 shows a close-up view of the foliage.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Magnolia* cultivar named 'MGPRO2008'. Data was collected in Waitara, New Zealand from 5 year old field grown plants. The time of year was Spring and the average temperature was 15° Centigrade during the day and 9° Centigrade at night. Color determinations are in accordance with The Royal Horticultural Society Colour Chart 2015 edition, except where general color terms of ordinary dictionary significance are used. The growing requirements are similar to the species. 'MGPRO2008' has not been tested under all possible conditions and phenotypic differences may be observed with variations in environmental, climatic, and cultural conditions, however, without any variance in genotype.

Botanical classification: *Magnolia* hybrid 'MGPRO2008'.
Use: Ornamental perennial.
Parentage: 'MGPRO2008' originated from the crossing of the female or seed parent *Magnolia* 'Amethyst Flame' and the male or pollen parent *Magnolia* 'Genie'.
Container size: 10 liter.
Vigor: Moderate.
Plant type: Small tree.
Growth habit: Bushy, spreading upward from base.
Plant shape: Upright, rounded.
Height: 1.5 meters in height.
Width: 1.2 meters in width.
Growth rate: 15 to 30 cm. per year.
Hardiness: −15° to 35° C.
Propagation: Field budding and tissue culture.
Crop time: 1 year from grafting.
Root: Fine and fibrous.
Stem:
- *Branching habit.*—Upright branching with branches less than 40 degrees from vertical.
- *Basal branching.*—Yes.
- *Number of lateral branches.*—4 to 5.
- *Lateral branch diameter.*—5 to 7 mm. in diameter.
- *Lateral branch length.*—30 to 50 cm. in length.
- *Internode length.*—20 to 70 mm. between nodes.
- *Stem color.*—N199A.
- *Stem aspect.*—Outward and upright.
- *Pubescence.*—Absent.
- *Stem shape.*—Round.
- *Stem texture.*—Smooth.
- *Stem strength.*—Moderate.
- *Pinching.*—Not required.

Foliage:
- *Leaf arrangement.*—Alternate.
- *Compound or single.*—Single.
- *Quantity of leaves per lateral branch.*—4 to 8.
- *Leaf shape.*—Ovate.
- *Leaf apex.*—Subacute.
- *Leaf base.*—Acute to rounded.
- *Leaf length.*—10.0 to 17.0 cm. in length.
- *Leaf width.*—4.5 to 10.0 cm. in width.
- *Pubescence.*—Absent on upper surface, sparse hairs on lower surface of new leaves.
- *Leaf texture.*—Both surfaces slightly leathery.
- *Leaf luster.*—Slightly glossy on both surfaces.
- *Leaf margin.*—Entire, slightly undulating.
- *Vein pattern.*—Pinnate.
- *Young leaf color* (*upper surface*).—146A.
- *Young leaf color* (*lower surface*).—147B.
- *Mature leaf color* (*upper surface*).—137A.
- *Mature leaf color* (*lower surface*).—137B.
- *Vein color* (*upper surface*).—137A.
- *Vein color* (*lower surface*).—146C.
- *Leaf attachment.*—Petiolate.
- *Petiole dimensions.*—14 to 20 mm. in length and 2 to 3 mm. in diameter.
- *Petiole color.*—146C to 146D.
- *Durability of foliage to stress.*—High.

Flower:
- *Flower arrangement.*—Solitary terminal cup to star shaped flowers.
- *Quantity of flowers per lateral stem.*—1.
- *Quantity of flower buds per lateral stem.*—1.
- *Quantity of flowers and buds per plant.*—Approximately 20 to 30.
- *Flowering habit.*—Flowers bloom in Spring before foliage appears and mid to late Summer with foliage.
- *Flowering season.*—Spring and mid to late Summer.
- *Time to flower or response time.*—5 to 7 weeks after breaking dormancy.
- *Fragrance.*—Slight fruity scent.
- *Self-cleaning or persistent.*—Self cleaning.
- *Flower bud length.*—20 to 25 mm. in length.
- *Flower bud diameter.*—10 to 15 mm. in diameter.
- *Flower bud shape.*—Narrow ovate to cordate.
- *Rate of bud opening.*—10 to 14 days.
- *Bud color.*—N78A to N78B.
- *Flower aspect.*—Upright and up to 30 degrees outward from vertical.
- *Flower shape.*—Star shaped.
- *Flower dimensions.*—14 to 17 cm. in diameter and 5 to 6 cm. in height.
- *Flower longevity.*—Lasts approximately 6 to 8 days on plant.
- *Flower longevity as a cut flower.*—Lasts approximately 6 days.
- *Tepal arrangement.*—Whorls of three.
- *Number of tepals.*—9.
- *Fused or unfused.*—Not fused.
- *Tepal shape.*—Ovate to obovate.
- *Tepal margin.*—Entire.
- *Tepal apex.*—Acuminate.
- *Tepal base.*—Cuneate.
- *Tepal texture.*—Smooth both surfaces.
- *Tepal luster.*—Slightly glossy both surfaces.

*Tepal dimensions.*—6.5 to 8.5 cm. in length and 2.5 to 3.5 cm. in width.

*Tepal color when opening* (*upper side*).—72B to 72C.

*Tepal color when opening* (*under side*).—N78A to NN78A.

*Tepal color when fully opened* (*upper side*).—72A to 72B.

*Tepal color when fully opened* (*under side*).—NN78B to NN78C.

*Tepal color fading to.*—72B to 72C.

Sepals: Absent.

Peduncle:

*Peduncle dimensions.*—6 to 10 mm. in length and 5 to 6 mm. in diameter.

*Peduncle angle.*—Curved upward to vertical.

*Peduncle strength.*—Strong.

*Peduncle pubescence.*—Absent.

*Peduncle color.*—138B suffused with N79B.

Reproduction organs:

*Stamen number.*—92 to 124.

*Anther shape.*—Curved upward.

*Anther Length.*—10 to 12 mm. in length.

*Anther color.*—72A base and outer side, inner side 72B.

*Amount of pollen.*—Low.

*Pollen color.*—4D.

*Pistil number.*—43 to 47 in number.

*Pistil length.*—13 to 15 mm.

*Stigma shape.*—Curved upward.

*Stigma color.*—64A.

*Ovary color.*—64A.

Fruit and seed production has not been observed to date.

Disease and pest resistance has not been observed to date.

The invention claimed is:

1. A new and distinct variety of *Magnolia* plant named 'MGPRO2008' as described and illustrated.

* * * * *